United States Patent
Rege et al.

(10) Patent No.: US 9,856,332 B2
(45) Date of Patent: Jan. 2, 2018

(54) METHODS FOR HIGH-THROUGHPUT IN-SITU MANUFACTURE OF USER DESIRED 3D POLYMERIC SCAFFOLDS

(71) Applicants: Kaushal Rege, Chandler, AZ (US); Taraka Sai Pavan Grandhi, Tempe, AZ (US); Andrew Dobos, Tempe, AZ (US)

(72) Inventors: Kaushal Rege, Chandler, AZ (US); Taraka Sai Pavan Grandhi, Tempe, AZ (US); Andrew Dobos, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/077,743

(22) Filed: Mar. 22, 2016

(65) Prior Publication Data
US 2016/0281056 A1 Sep. 29, 2016

Related U.S. Application Data

(60) Provisional application No. 62/137,134, filed on Mar. 23, 2015.

(51) Int. Cl.
| | |
|---|---|
| *C12M 1/16* | (2006.01) |
| *C08F 10/00* | (2006.01) |
| *C12M 1/12* | (2006.01) |
| *C12N 5/00* | (2006.01) |

(52) U.S. Cl.
CPC ............. *C08F 10/00* (2013.01); *C12M 25/14* (2013.01); *C12N 5/0068* (2013.01)

(58) Field of Classification Search
None
See application file for complete search history.

(56) References Cited

U.S. PATENT DOCUMENTS

| | | | | |
|---|---|---|---|---|
| 2014/0079752 | A1* | 3/2014 | Huebsch | A61L 27/26 424/422 |
| 2015/0283073 | A1* | 10/2015 | Tang | A61K 47/10 424/85.2 |
| 2016/0228611 | A1* | 8/2016 | Castro | A61L 27/48 |
| 2017/0115275 | A1* | 4/2017 | Rege | G01N 33/5008 |

OTHER PUBLICATIONS

Lee, H. et al. Fabrication and Characteristics of Antiinflammatory Magnesium Hydroxide Incorporated PLGA Scaffolds Formed with Various Porogen Materials. Macromolecular Research 22(2)210-218, Feb. 2014.*
Flaibani M. et al. Gas Antisolvent Precipitation Assisted Salt Leaching for Generation of Micro and Nano Porous Wall in Biopolymeric 3D Scaffolds. Materials Science and Engineering C 32(6)1632-1639, 2012.*
Mi H. et al. Fabrication of Porous Synthetic Polymer Scaffolds for Tissue Engineering. J of Cellular Plastics 51(2)165-196, 2015.*
Nam et al., A novel fabrication method of macroporous biodegradable polymer scaffolds using gas foaming salt as a porogen additive., Journal of Biomedical Materials Research, 2000, 53(1():1-7.
Yang et al., Synthesis and application of a macroporous boronate affinity monolithic column using a metal-organic gel as a porogenic template for the specific capture of glycoproteins., Journal of Chromatography A, Dec. 2011, 1218(51):9194-9201.
Grandhi et al., Aminoglycoside Antibiotic-Derived Anion-Exchange Microbeads for Plasmid DNA Binding and in Situ DNA Capture., ACS Applied Materials & Interfaces, Nov. 2014, 6(21):18577-18589.
Grandhi et al., Design of Bone Microenvironment Mimicking Antibiotic-based Hydrogels for Generation of Three Dimensional Tumor Models of Dormancy and Relapse., ASU Society for Biomaterials, Abstract, 2014.
Lozinsky et al., Polymeric cryogels as promising materials of biotechnological interest., Trends in Biotechnology, Oct. 2003, 21(10): 445-451.
Szot et al., 3D in vitro bioengineered tumors based on collagen I hydrogels., Biomaterials, 2011, 32(31):7905-7912.
Derda et al., Paper-Supported 3D Cell Culture for Tissue-Based Bioassays., Proceedings of the National Academy of Sciences of the United States of America, Nov. 2009, 106(44):18457-18462.
Elliot et al., A review of three-dimensional in vitro tissue models for drug discovery and transport studies., Journal of Pharmaceutical Sciences, Jan. 2011, 100(1):59-74.
Kim et al., Three-dimensional in vitro tissue culture models of breast cancer—a review., Breast Cancer Research and Treatment, Jun. 2004, 85(3):281-291.
Mueller-Klieser, Tumor biology and experimental therapeutics., Critical Reviews in Oncology and Hematology, 2000, 36(2):123-139.
Keskar et al., In vitro evaluation of macroporous hydrogels to facilitate stem cell infiltration, growth, and mineralization., Tissue Engineering—Part A, Jul. 2009, 15(7):1695-1707.
Sykova et al., Bone Marrow Stem Cells and Polymer Hydrogels—Two Strategies for Spinal Cord Injury Repair., Cellular and Molecular Neurobiology, Nov. 2006, 26(7):1111-1127.
Murphy et al., Salt fusion: An approach to improve pore interconnectivity within tissue engineering scaffolds., Tissue Engineering, 2002, 8(1):43-52.
Liu et al., Polymeric Scaffolds for Bone Tissue Engineering., Annals of Biomedical Engineering, Mar. 2004, 32(3):477-486.
Xiong et al., Synaptic transmission of neural stem cells seeded in 3-dimensional PLGA scaffolds., Biomaterials, Aug. 2009, 30(22):3711-3722.

(Continued)

*Primary Examiner* — Ralph J Gitomer
(74) *Attorney, Agent, or Firm* — Gavin J. Milczarek-Desai; Quarles & Brady LLP

(57) ABSTRACT

Biomedical devices and methods are disclosed for the development of 3D polymeric scaffolds for cell culture, high throughput screens for biomolecule purification, and generation of bone mimetic materials. The devices may feature multiple geometries, and scaffold generation capabilities include multiple gel types utilizing organic and aqueous phase pregel. Additionally, macroporous and non-macroporous morphologies are possible.

20 Claims, 24 Drawing Sheets

(56) References Cited

OTHER PUBLICATIONS

Lin et al., Preparation of macroporous biodegradable PLGA scaffolds for cell attachment with the use of mixed salts as porogen additives., Journal of Biomedical Materials Research, 2002, 63(3):271-279.

Guan et al., Preparation and characterization of a highly macroporous biodegradable composite tissue engineering scaffold., Journal of Biomedical Materials Research Part A, Dec. 2004, 71A(3):480-487.

* cited by examiner

Fig 6a. 10 µL Amikalith I column pDNA binding
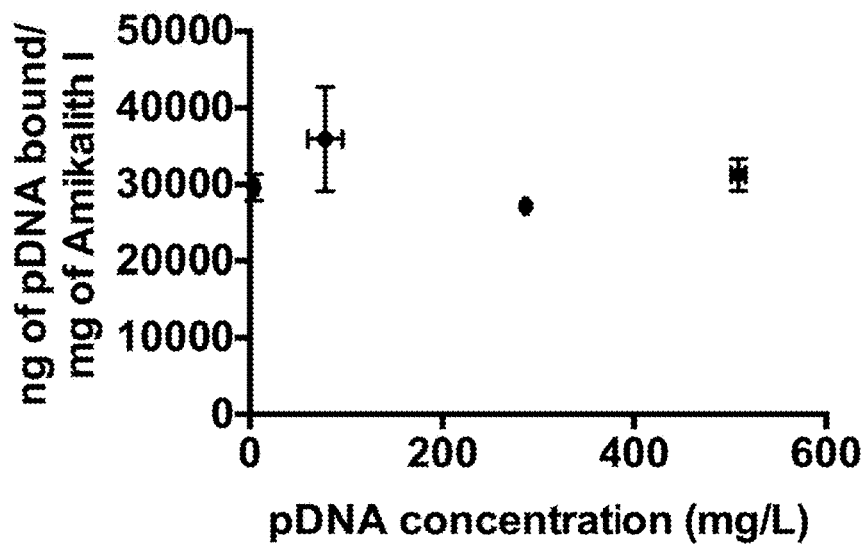
Fig. 6b. 25 µL Amikalith I column pDNA binding
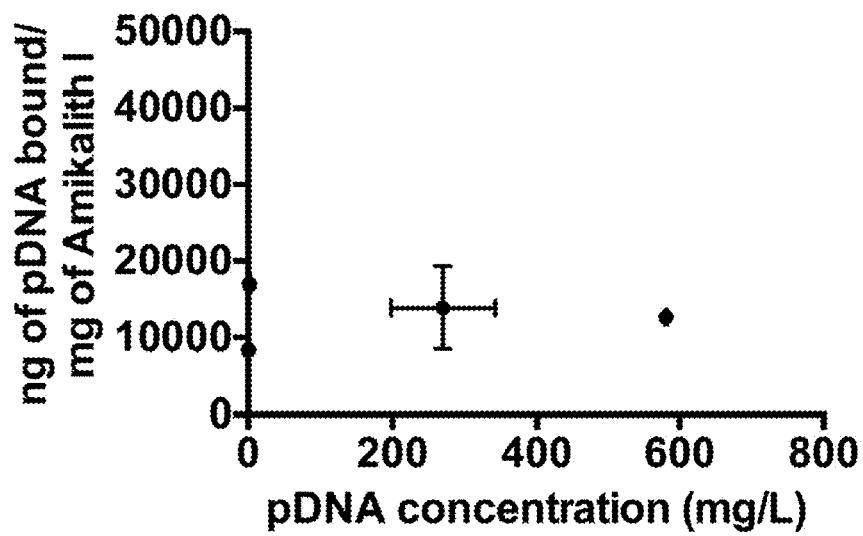

Fig. 6c

| Amikalith I | 10 µL columns | 25 µL columns |
|---|---|---|
| pDNA binding at 25°C in 10 mM Tris-Cl buffer | 36,363 ng of pDNA/mg of Amikalith | 14,016 ng of pDNA/mg of Amikalith |

METHODS FOR HIGH-THROUGHPUT IN-SITU MANUFACTURE OF USER DESIRED 3D POLYMERIC SCAFFOLDS

CROSS REFERENCE

This application claims priority to U.S. provisional patent application 62/137,134 filed on Mar. 23, 2015, which is incorporated by reference herein in its entirety.

FEDERALLY SPONSORED RESEARCH OR DEVELOPMENT

This invention was made with government support under 1067840 awarded by the National Science Foundation. The government has certain rights in the invention.

FIELD OF THE INVENTION

Biomedical devices for the development of 3D polymeric scaffolds for stem/cancer cell culture and high throughput adsorbent screens for biomolecule purification and generation of bone mimetic materials.

BACKGROUND OF THE INVENTION

Cells in human body associate with neighboring cells and tissues in three dimensions, but the laboratory cell culture techniques used to mimic the same in-vivo processes rely on two dimensional cell culture plates. Cells grown on these 2D plates do not mimic the human body. They lack extensive cell-cell contact, nutrient and metabolite gradient, and the complex waste disposal system that exists in the body. Hence it is required to capture the 3D nature of human body in "the petridish" of the research lab.

SUMMARY OF THE INVENTION

The embodiments herein relate in general to biomedical devices for the development of 3D polymeric scaffolds for stem/cancer cell culture, high throughput adsorbent screens for biomolecule purification, and generation of bone mimetic materials for in-vitro prostate cancer dormancy and relapse.

In certain embodiments, devices (e.g., EZGEL Apparatus) and novel methods for high throughput fabrication of macroporous hydrogel/polymeric monoliths incorporating a multicomponent design are disclosed.

In addition to multiple geometries for the devices, scaffold generation capabilities are diverse. For example, a polymeric scaffold can be made utilizing multiple gel types, with organic and aqueous phase pregel, including Amikagel, PLGA and collagen. In addition, both macroporous and non-macroporous morphologies are possible.

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

BRIEF DESCRIPTION OF THE DRAWINGS

The invention will be better understood from a reading of the following detailed description taken in conjunction with the drawings in which like reference designators are used to designate like elements, and in which:

FIGS. 6a, 6b, and 6c, graphically show that The plasmid DNA binding ability of Amikalith I did not increase with increase in weight/column of Amikalith I (n=2). It is likely that poor interconnectivity among pores in Amikalith I, the inner surfaces of the gel are inaccessible to the pDNA for binding;

DETAILED DESCRIPTION OF THE PREFERRED EMBODIMENTS

Figure 1A:
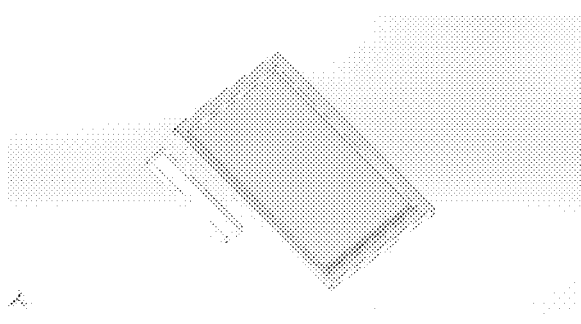
FIGS. 1a, b, c, d, e, and f, illustrate a) First (D1) b) Second (D2) c-d) Third (D3) generation acrylic designs for the generations of Amikaliths. Third generation of the acrylic was found to be the best in terms of ease of Amikalith generation. c-d) Mirror pieces of acrylic geometries with semicircular teeth design were combined to form a central circular gap to allow for sodium chloride addition and subsequent Amikagel pre-gel wetting. e-f) Insets to increase the throughput of the device are shown. These insets have semi-circular teeth on both sides and attach to the end pieces to increase the throughput/device.

The disclosure herein is described in preferred embodiments with reference to the figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Macroporous scaffolds provide a 3D substrate that matches the 3D environment the cells in the body reside in. In addition, these macroporous scaffolds can be designed to be extensively interconnected, mimicking the bone trabecular structure. Bone trabeculae are characterized with a highly porous structure filled with bone marrow. Multiple macroporous material have been used to create bone mimics that can capture stem cell growth and differentiation on them etc. These macroporous materials are made by using a porogen such as salt/glucose or sucrose, etc., which are insoluble in polymer slurry, but are soluble in aqueous solvents. The polymer pre-gel is mixed with insoluble salt crystals and casted on a special device. Polymerization is initiated either by a catalyst or an enzyme added to the pre-gel mixture. Heat and light are also used to initiate polymerization. Once the polymerization and gelation are complete, the porogen is leached out using aqueous solvents such as water, leaving behind a macroporous scaffold.

A significant challenge in this approach is the absence of a device that can be used to create these systems in high throughput. Applicants found existing technologies to be tedious and poor in yield. A critical problem exists in easy recovery of the polymeric macroporous scaffold after its preparation. Hence, Applicants designed and developed devices that can be used by global research community working with macroporous gels for biomedical engineering research. The devices allow for generation of user-desired macroporous polymeric scaffolds in high-throughput.

EXAMPLE

Design and Selection of Acrylic Geometry for Successful Macroporous "Amikagel"

The main purpose of the acrylic device design in this example was for preparation and high-throughput generation of "Amikaliths"—3D macroporous amikagels, referred to as 'Amikaliths' from now on. Amikagels are aminoglycoside based hydrogels developed in our lab. The amines on the surface of the amikagels were exploited for plasmid DNA (pDNA) binding by converting them into a microbead morphology. Applicants hypothesized that monomers used for synthesizing Amikagels could be reacted around salt crystals (porogen) in a column, followed by salt leaching in nanopure water to prepare Amikaliths. Salt leaching methods of macroporous column generation is a widely popular method of 3D macroporous gel formation. The leached salt would give rise to macroporous gaps in the hydrogel column that can be used for pDNA binding and elution studies. Other porogens that could be used include sucrose/glucose/sugar etc.

Towards that goal, Applicants wanted to develop an assistive device technology that can generate large number of Amikaliths with ease (High-throughput). Our previous findings strongly indicated that Amikabeads (Amikagel microbeads) are novel materials for pDNA binding and recovery equivalent to commercially available systems. In addition, Applicants have also shown that Amikagels (Amikagel macrogels) support the culture of prostate cancer dormant phenotype and relapse in high throughput 96 well plates.

There is a need to generate Amikaliths in high-throughput. Firstly, macroporous Amikaliths could mitigate the requirement of high pressure to operate mobile phase through Amikabead filled columns. Monolithic structures provide an alternative work around to the problem of the need of high-pressure chromatographic operation without compromising the surface area.

Secondly, the hydroxyl and amine rich surface of Amikaliths offer unique opportunities to conjugate pseudo-affinity ligands to the surface to improve the selectivity of the substrate towards pDNA binding. Generation of Amikaliths in high-throughput will allow screening of multiple pseudo-affinity ligands towards improvements in pDNA binding and elution. Thirdly, in the field of prostate cancer dormancy and relapse, these macroporous monolithic structures could be used to mimic bone trabeculae. Generation of macroporous Amikaliths in high-throughput will allow identification of cellular response to these gels. In addition, these could be used as a tool for large-scale drug screens to identify novel drugs against important cancer phenotypes such as dormancy and relapse.

Hence, Applicants wanted to generate Amikaliths in high-throughput using a reproducible method. Our initial trials to generate Amikaliths using 96 well plates yielded extremely poor results.

Figure 1B:
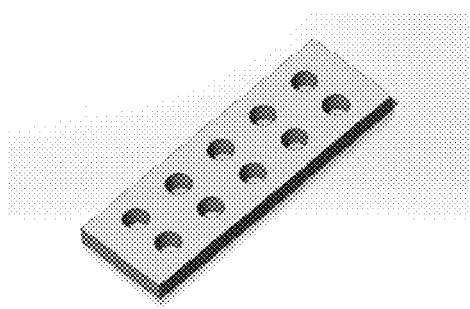
Figure 1C:
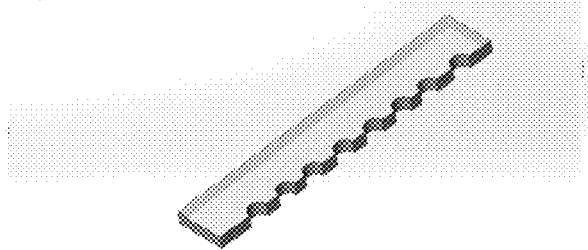

To overcome the challenge, Applicants decided to fabricate a device/s for high-throughput development of the gel. As shown in FIG. 1, Applicants utilized acrylic sheets to cut out different design geometries, and tested them for high-throughput Amikalith generation. FIGS. 1a-b. show the first and second version of acrylic designs for high-throughput Amikalith generation. The first generation of the acrylic design D1 involved filling of the plate with salt crystals to the extent required. The sliding stick was used to vary the amount of salt used in the system. Once the required amount of salt was added to the column, the salt was wet with the pre-gel solution. Upon leaching of the salt, a sheet of macroporous Amikalith was obtained, out of which the required number of discs were cut out using the laser. The main drawback in the first generation acrylic design D1 was its high need of raw materials along with high amount of wastage to obtain the Amikaliths. However, this design could be useful for generation of macroporous sheets of gel if needed.

In order to overcome the limitations of the first generation of acrylic design D1, a second design was developed. An inverse of design D1, gave rise to design D2 (FIG. 1b), where Applicants proposed the generation of gels within the cylindrical cavities. The cavities could be filled up with salt, leading to in-situ gelation and experimentation. Although the gelation was satisfactory, the recovery of columns from the device proved tricky. The second-generation acrylic design was plagued with issues of less recovery of fully formed Amikaliths. Learning from the previous two generations, Applicants designed the third generation of Acrylic geometry (FIGS. 1c-d), which showed very high success in high throughput generation of Amikaliths.

Figure 1D:
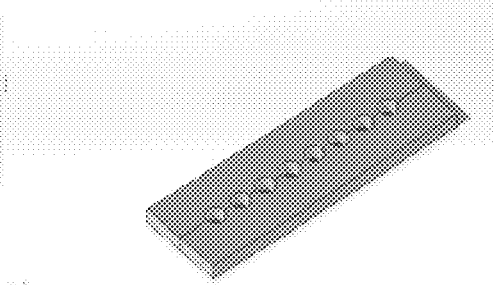
Figure 2A:
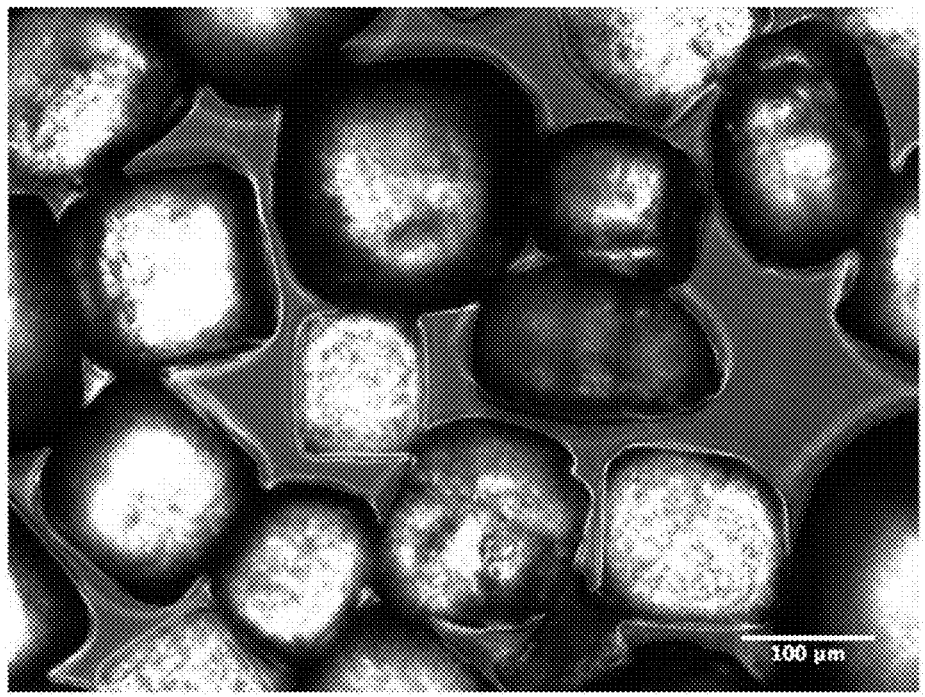
FIG. 2a shows Fused salt crystals of average size after incubation in a 37° C. incubator with ~95% humidity for 3 hours. Fused crystals can be seen to merge with each other.
Figure 2B:
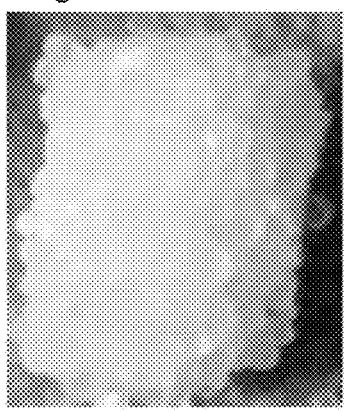
FIG. 2b illustrates fusion of salt crystals achieved by incubation in the humidified chamber for 3 hours gave rise to a fused salt column, which was used to generate Amikagel II.
Figure 3:
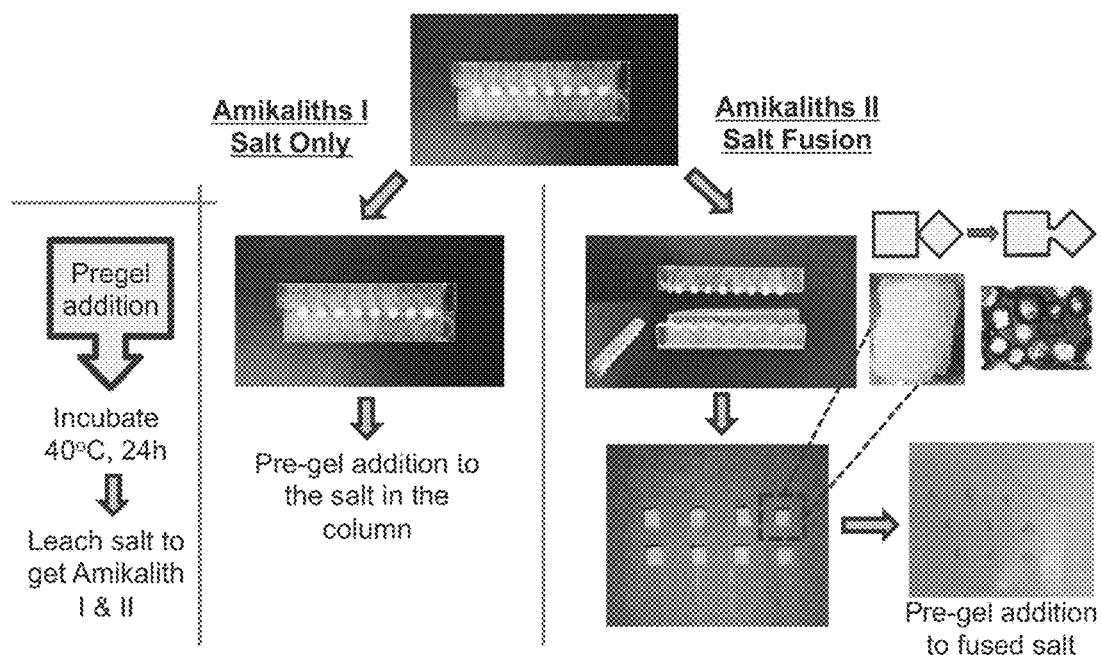
FIG. 3 illustrates a process of Amikaliths I and II generation using the EZGel Apparatus.

Third generation of acrylic design consisted of two mirror pieces with semi-circular teeth (diameter—0.12 inches) that could be linked to each other to generate one unit (FIG. 1d). Both cylindrical pieces were wrapped with a layer of parafilm for easy assembly and disassembly. The cylindrical gap created by assembling the unit was filled with sodium chloride crystals and used for high-throughput generation of Amikaliths (FIG. 2-3). One of the bases was sealed with paraffin film to prevent salt from falling out. The salt was then wet with pre-gel solution prepared in DMSO, followed by its incubation for gelation. After gelation, the recovery of gels was found to be very easy due to its unique design.

One of the greatest strengths of this device is the central break-line that can easily disassemble the pieces of the device after the gelation. Usage of parafilm made the task of breakage very easy. The gels tended to stay unbroken during their recovery due to the unique design of the device. This third generation acrylic design was found to be far superior compared to other two previous generations in its ease of use and the reproducibility for Amikalith production. The entire method has been tested at the hands of at least two/three independent operators across more than 25-30 independent experiments (n>25).

Figure 1E:
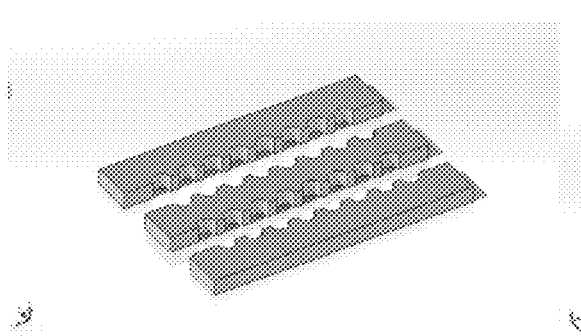
Figure 1E:
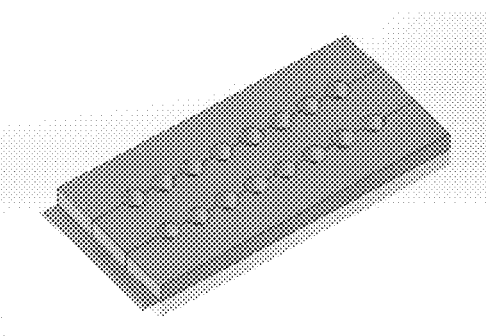
Figure 1F:
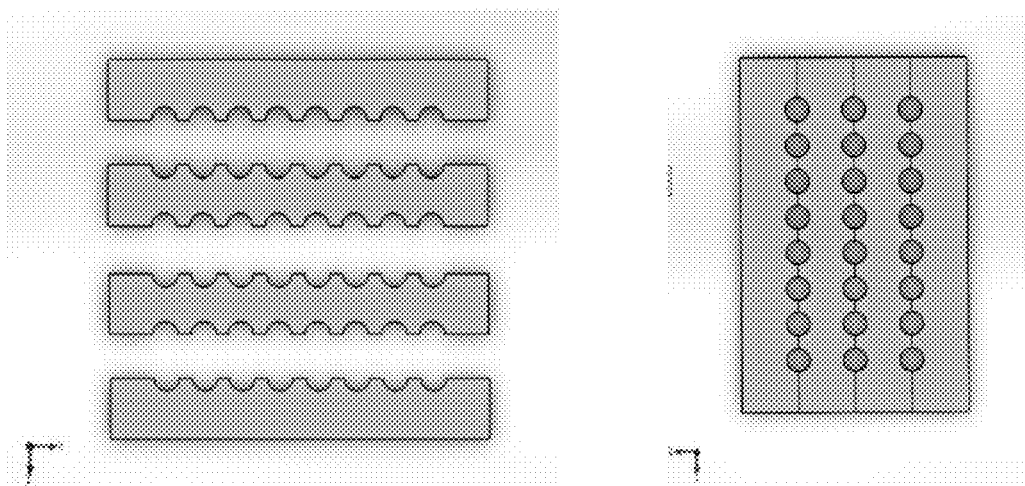

Additional design insets were created to increase the throughput of the device. As shown in FIG. 1e-f, multiple additional insets were developed to add to the existing device. The insets have semi-circular teeth on both sides and can be joined in between the two end pieces of the existing device. These insets were greatly able to increase the throughput of the device.

The same device can be made of any dimension, user desired teeth shape, and any height of the column. The device is currently made of acrylic using a laser cutter, but can be made using multiple materials such as wood, steel, glass, polypropylene etc. 3D macroporous Amikagels were developed as the first proof of concept with this device, after which, its use was further expanded to other polymeric gels such as PLGA.

Figure 4A:
FIG. 4a is a photograph of 3D macroporous PLGA matrices. Fused salt columns were wetted with PLGA in chloroform (100 mg/mL) and incubated at 40° C. for 2 hours.
Figure 4B:
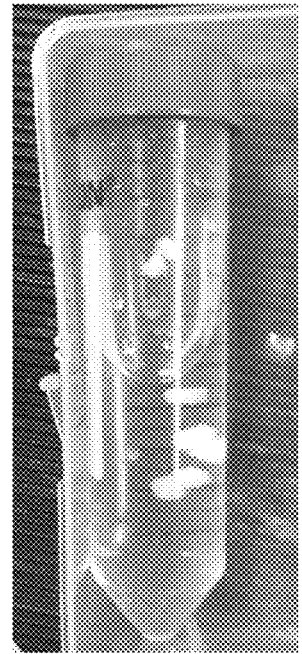
FIG. 4b illustrates wash steps to generate PLGA matrix.
Figure 4C:
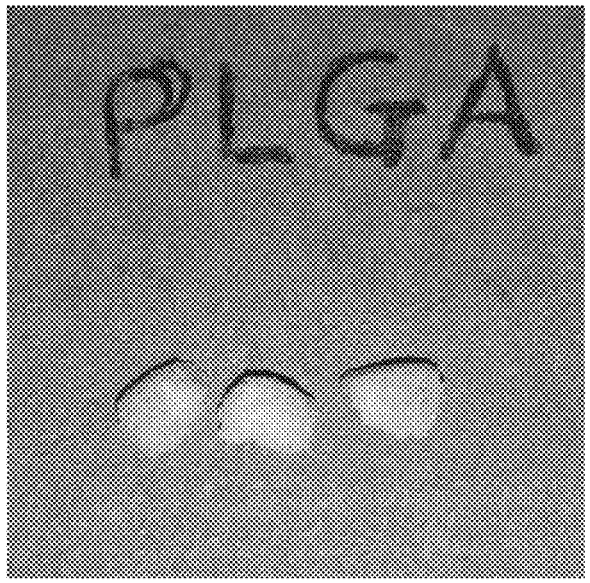
FIG. 4c is a photograph of macroporous PLGA matrices obtained using Applicants' technology.

Salt was used as a porogen to prepare Amikaliths and PLGA 3D scaffolds. Pore sizes of the columns can be easily controlled by using the porogen of appropriate diameter. Additional porogens including sucrose, glucose can also be used to prepare the columns. In addition, multiple organic solvents can be used to prepare the gel, such that they do not dissolve the porogen or the device. Naturally occurring gels including collagen, fibronectin, and peptide gels can also be made using this technology. FIG. 4a-c shows the preparation and manufacture of macroporous PLGA matrices using our new technology. Once fused salt columns were obtained using our technology, PLGA dissolved in chloroform (100 mg/mL) was applied to the fused salt columns. Once the columns were wetted, they were incubated in 40° C. incubator for 2 hours, followed by multiple wash steps to remove the salt. PLGA macroporous gels find their use in multiple 3D cell culture streams mimicking human tissues. Macroporous PLGA scaffolds have been used to generate artificial neural network in vitro, substrates for cell attachment, substrates for bone tissue engineering. In addition, PLGA polymer is FDA approved due to its controlled biodegradability into non-toxic units of lactic acid and glycolic acid in vivo. Successful manufacture of macroporous 3D PLGA matrices shows that the current EZGel Apparatus system can be employed to generate macroporous gels with different user desired polymeric systems.

Below is the detailed description of the method used to develop Amikaliths I and II. The method of their development is unique.

Generation of Amikaliths—I and II

As discussed above, salt crystals were used as porogens to generate the Amikaliths. 300 mg of salt crystals (cubes) of three different average edge lengths of ~320, 520 and 640 μm were added to the circular gap in the acrylic geometry and wetted with 10 μL Amikacin-PEGDE in DMSO and incubated for 24 hours. The paraffin film coating on the acrylic allowed for very easy disassembly and recovery of gel-salt columns after gelation. Recovery of intact gel-salt columns in absence of paraffin film was very difficult and tedious. Amikaliths generated using salt crystals without any further modifications were termed as Amikaliths I. Amikaliths I prepared using salt alone did not show any interconnections between the salt crystals as observed using the confocal images. It is likely that the salt crystals get completely covered by pre-gel during its addition and gelation occurs between the spaces among the salt crystals. Hence, it is likely that the gel will be poorly interconnected.

Fusion of salt crystals could allow for the formation of interconnected pores. Salt fusion for the generation of interconnected pore structure in 3D gels has been used before. Amikaliths-II were designed to harness the salt fusion capability. Salt crystals were fused with each other by placing the acrylic geometries filled with salt in a 37° C. incubator with ~95% humidity for 3 hours. FIG. 2a shows the salt crystal columns obtained after salt fusion.

Such intact columns were not obtained in absence of proper salt fusion. Fusion of salt with 2 hours incubation allowed for the recovery of fused salt columns from the device which were further wet with pre-gel. FIG. 2b shows the phase contrast image of fused monolayer of salt crystals after just 3 hours of incubation. FIG. 3. shows the entire process of generation of Amikaliths II using the salt fusion technology. Briefly, both the acrylic end pieces were covered with parafilm and joined together. Pressure was applied so that both the pieces stick to each other. One side of the device was covered with parafilm so as to provide a base.

Next, salt crystals (cubes) with different average edge lengths were filled into the columns. Once the columns were filled, they were cleaned to remove excess salt. Then, the entire device was placed in the 95% humidity chamber to initiate salt fusion. After 3 hours, the device was taken out and allowed to dry at room temperature for 12 hours. Once dried, the device was cracked in the middle and the salt columns were carefully removed using a 27 G needle. Recovered salt fusion columns were then wetted with 10 µL pre-gel solution. Gelation was initiated by placing the salt columns at 40° C. incubator for 24 hours after which the salt columns were immersed in water to get rid of salt. The salt columns were washed three times prior to their usage.

Plasmid DNA binding was used to assess the binding surface area differences among the three Amikaliths. Amikalith surface is rich in primary amines, which are positively charged at pH 8.5 and has been shown to bind pDNA. FIG. 3 shows the composition of Amikaliths I and II. Amikaliths II prepared using fused salt crystals were in general poor in mechanical stiffness compared to Amikaliths I.

pDNA Binding to Amikalith I and II pDNA binding to the Amikaliths I and II prepared using three different salt sizes was investigated. Amikaliths were incubated with 45000-300,000 ng of pDNA for 24 hours. FIGS. 4a and b show the qmax values for pDNA binding on Amikaliths I and II generated using 520 µm salt crystals. Amikabeads I and 2 do not differ significantly in their pDNA binding ability. Amikaliths generated using salt crystals of 520 µm showed a marginally higher pDNA binding ability compared to other sizes. Overall, Amikaliths were comparable to Amikabeads in their pDNA binding ability.

Figure 5A:
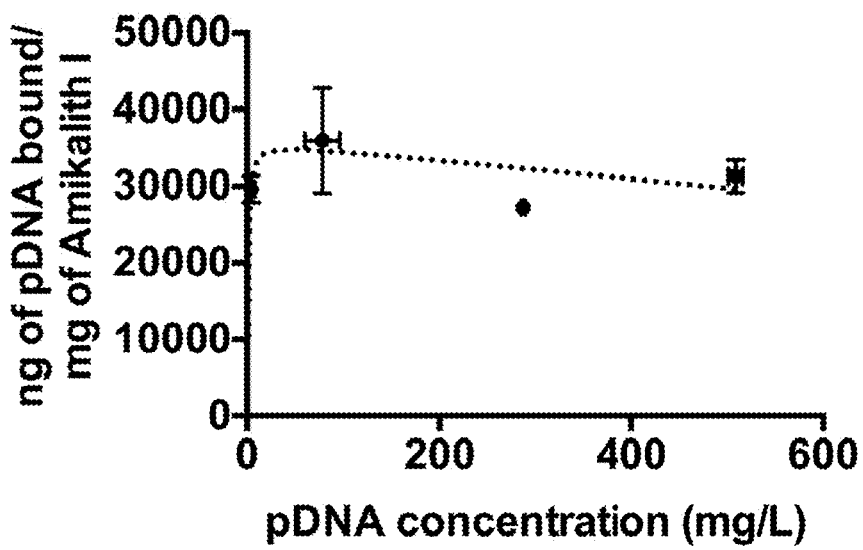
FIG. 5a graphically illustrates pDNA binding to Amikaliths I using 520±170 µm salt crystals.
Figure 5B:
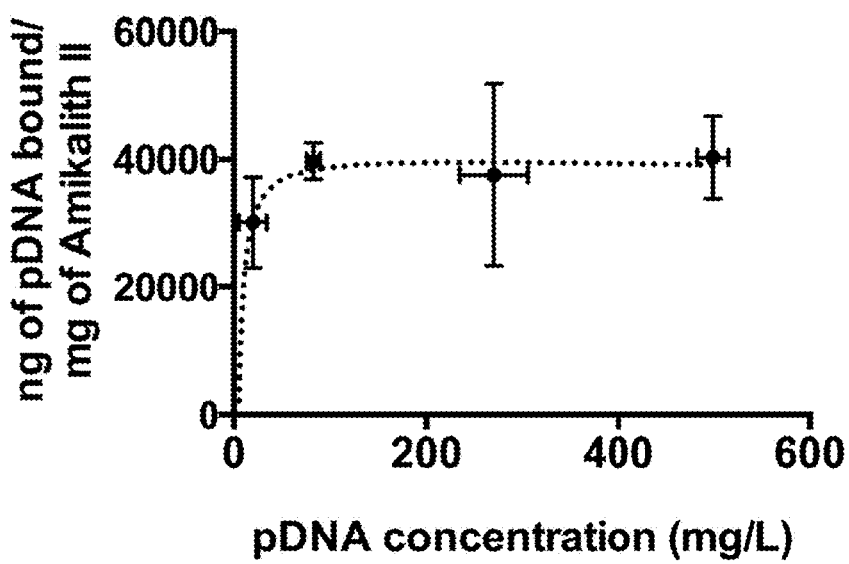
FIG. 5b graphically illustrates pDNA binding to Amikaliths II using 520±170 µm salt crystals.
Figure 5C:
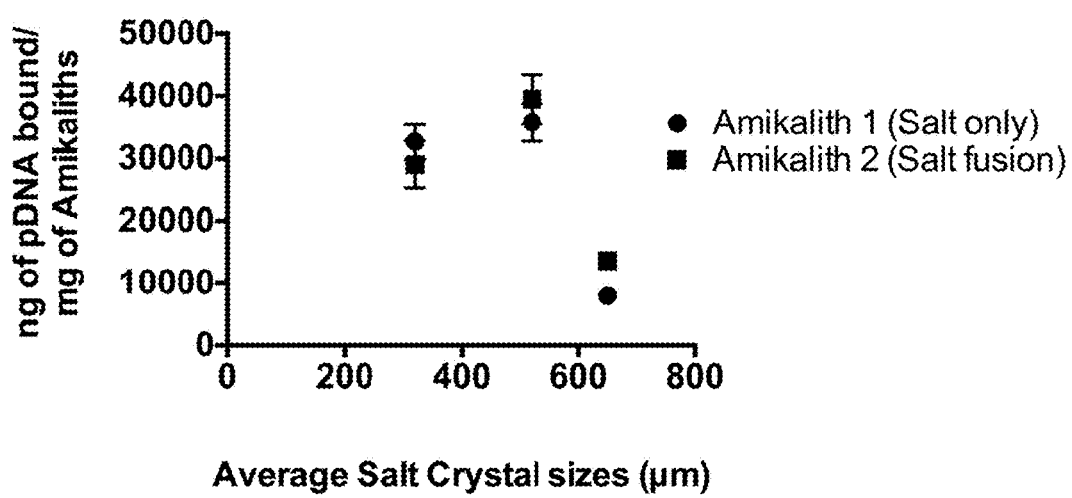
FIG. 5c graphically illustrates Qmax values calculated using Langmuir adsorption isotherm for pDNA binding to Amikalith I and II prepared using three different salt crystal sizes.
Figure 7A:
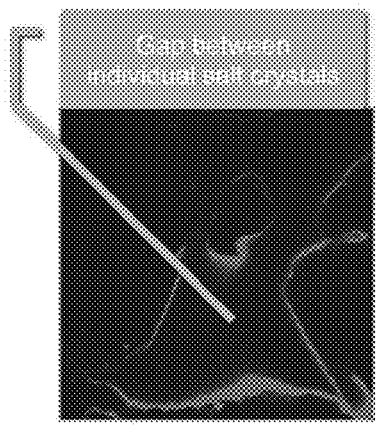
FIG. 7a illustrates that Plasmid DNA location in Amikalith I could be used to trace the surface characteristics of the column. Interconnections were not found in Amikalith I as indicated in the image.
Figure 7B:
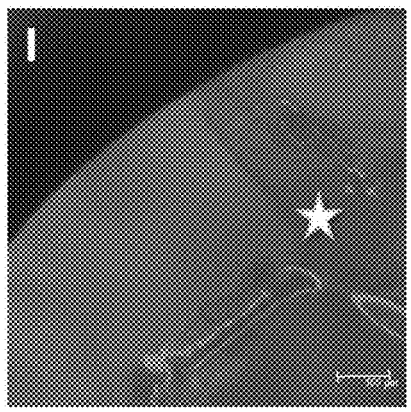
FIG. 7b I, II, III, and IV, show different z-stacks of pDNA bound Amikalith II show the structures of interconnected pores. Interconnected pores were not observed in images taken for Amikalith I.
Figure 7B:
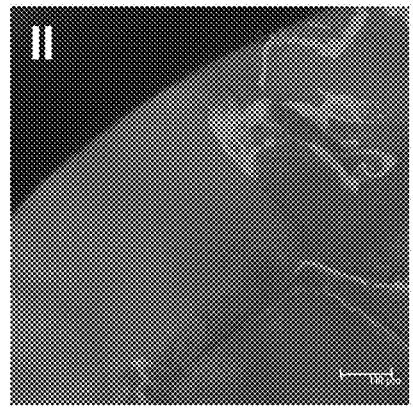
Figure 7B:
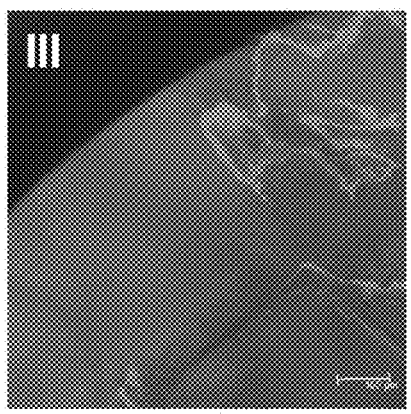
Figure 7B:
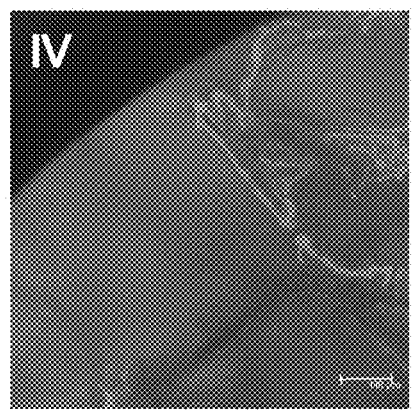

Amikaliths prepared with higher salt crystal diameter to 650 µm showed lower pDNA binding capacities compared to the ones prepared using smaller crystals of 520 µm (FIG. 5c). It is likely that at equal weights, higher diameter salt crystals could mean lower surface area leading to a decrease in binding.

As shown in FIG. 6, increase in the weight/monolith in Amikalith I did not cause a proportional increase in the overall binding profile of the monolith. It is likely that Amikalith I due to its non-interconnected pore structure, doesn't improve overall area available for binding with an increase in the weight.

Figure 8A:
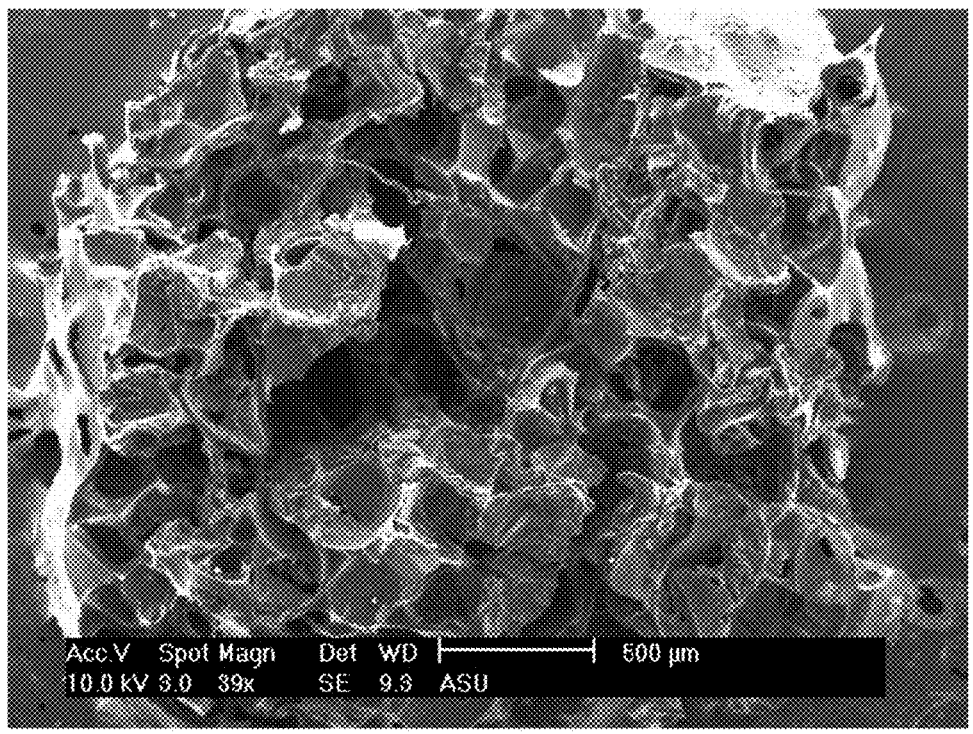
FIGS. 8a and 8b are SEM images of Amikalith I and II showing macroporous structures.
Figure 8B:
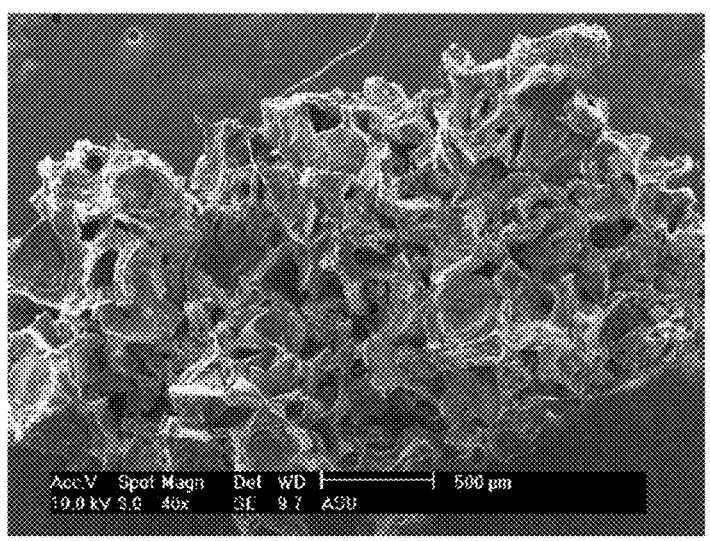

As seen in FIGS. 7 and 8, the Amikaliths I showed no interconnectivity among pores whereas Amikalith II showed interconnections among the pores. FIG. 7b shows confocal images of Amikalith II with changing z-height. The blue line indicates the interconnections among the pores as the z-height is changed. However, these interconnections did not provide any differences in the binding of the Amikaliths I and II.

Doxorubicin Conjugation to Amikabeads and Amikaliths

One application of the Amikaliths is to provide a high surface area material with provision to attach multiple pseudoaffinity ligands to its surface. Doxorubicin is a very well known anticancer drug, which works by binding to the DNA double helix and prevents cell duplication. Conjugation of DNA binding drugs such as doxorubicin, mitoxantrone to the surface of Amikaliths could be used as new source of pDNA binding ligands.

Figure 9A:
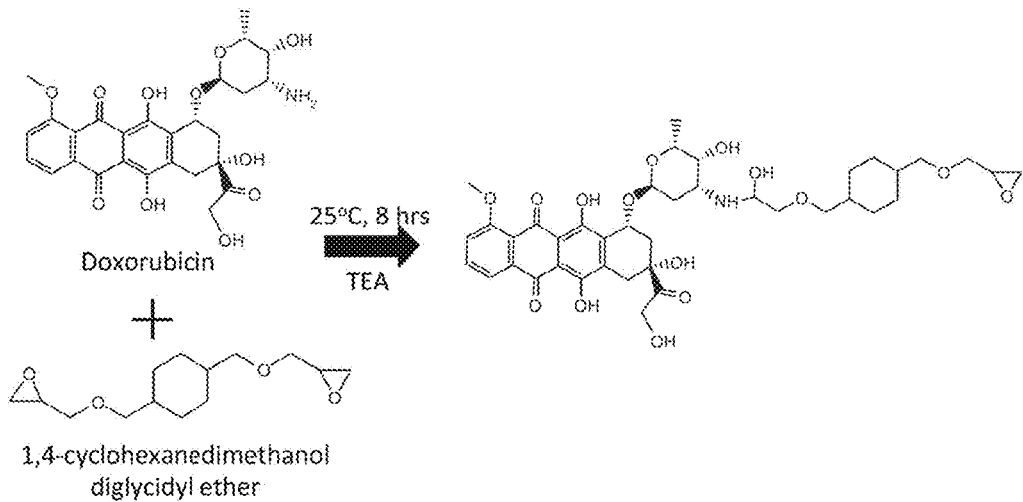
FIG. 9a shows a reaction scheme wherein Doxorubicin was stirred with 1,4-cyclohexanedimethanol diglycidyl ether with Triethylamine (1:3:5) in DMSO for 8 hours at 25° C.
Figure 9B:
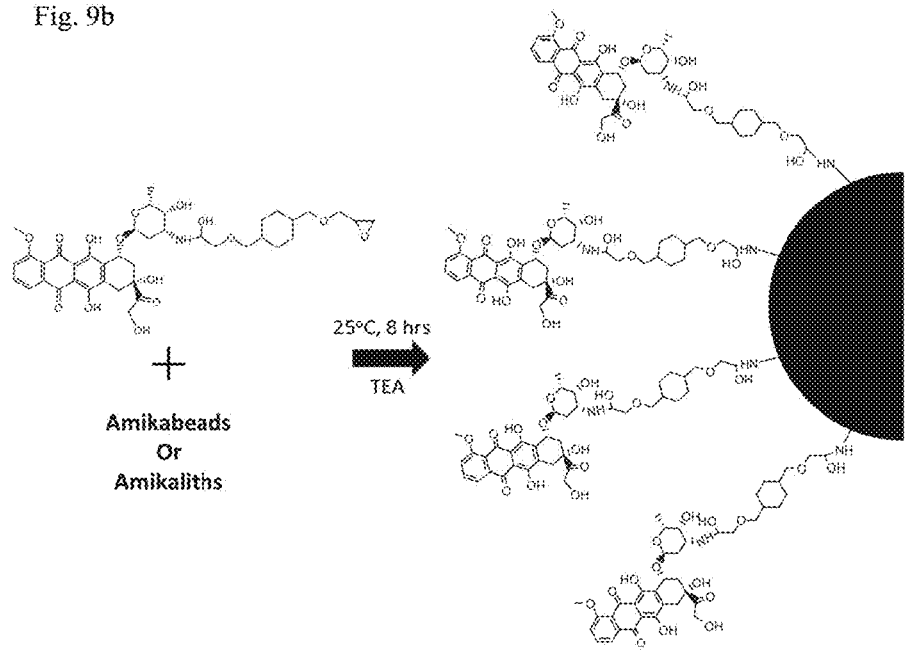
FIG. 9b illustrates that the Amikabeads/Amikaliths were added to the mixture for 8 hours followed by extensive washing steps to remove unreacted doxorubicin.
Figure 9C:
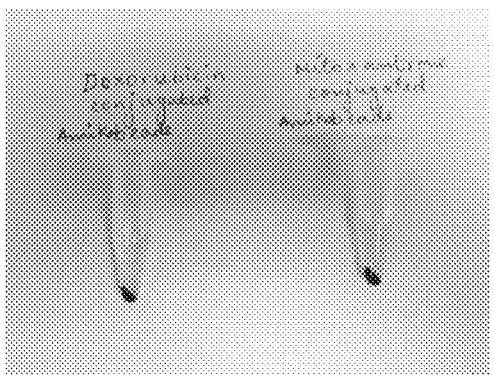
FIGS. 9c and 9d illustrate Doxorubicin and Mitoxantrone conjugated microbeads.
Figure 9D:
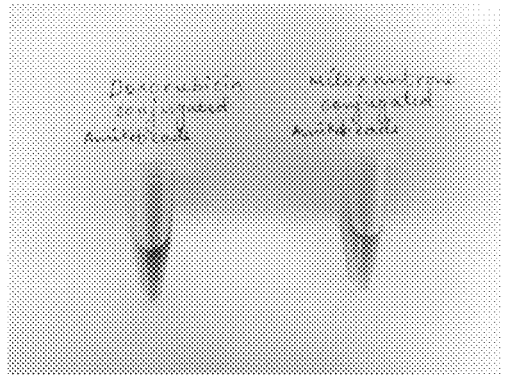
Figure 9E:
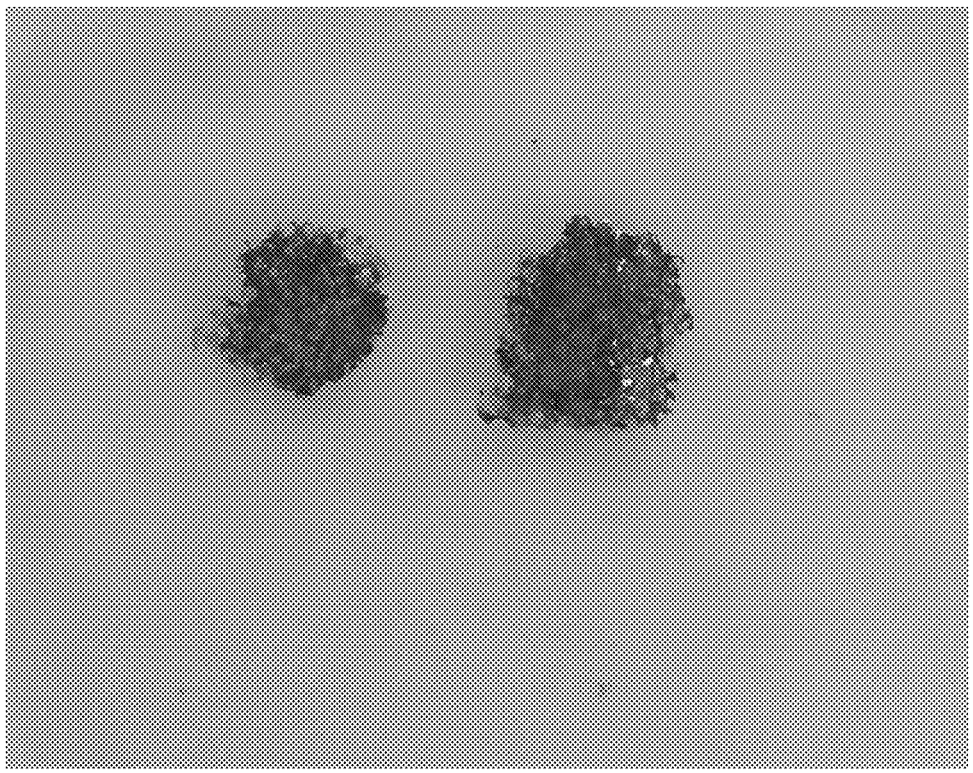
FIG. 9e illustrates Doxorubicin conjugated monoliths.
Figure 10A:
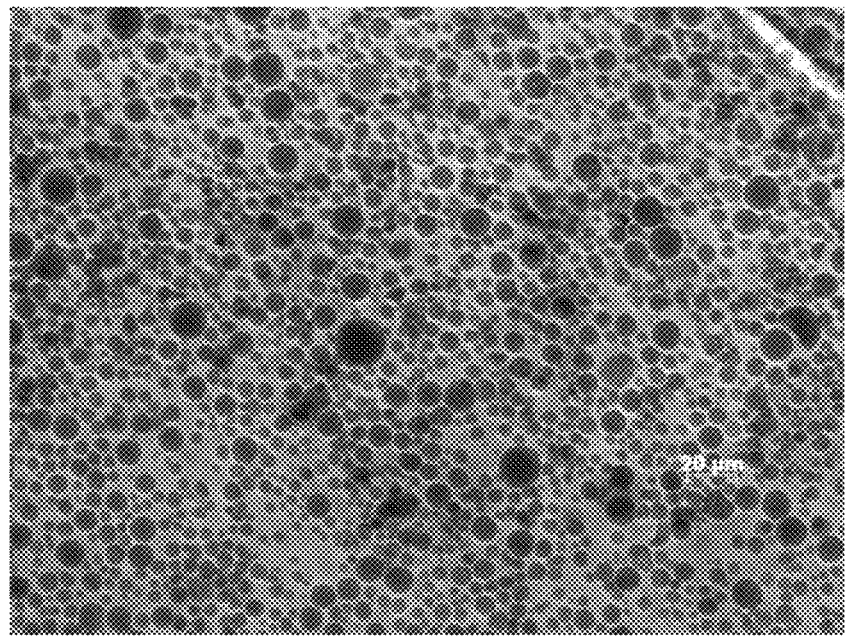
FIG. 10a is photograph illustrating that conjugating 1,4-CHDDE to doxorubicin followed by addition of the intermediate to the beads gave rise to minimal clumping and uniform conjugation.
Figure 10B:
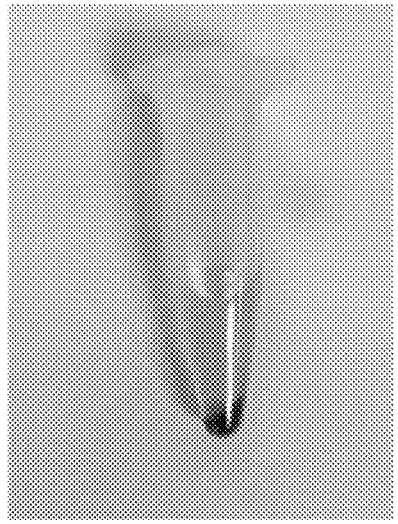
FIG. 10b illustrates that Doxorubicin (Red) conjugated Amikabeads (pellet) were generated for their studies in plasmid DNA binding.

As a proof of concept, Applicants attached anticancer drug doxorubicin to the surface of Amikabeads (Microbeads version of Amikagels, previously published). As shown in FIG. 9, excess 1,4 cyclohexanedimethanol diglycidyl ether was used to link one doxorubicin/Mitoxantrone to one of the epoxy ends of the cross-linker. Next, Amikabeads/Amikaliths were added to the solution and the other end of the epoxy was conjugated to the amines on the beads. FIG. 9c-e shows the drug conjugated Amikabeads and Amikaliths after the conjugation process. The process also gave rise to non-clumped beads after the final conjugation step (FIG. 10a-b).

Figure 10C:
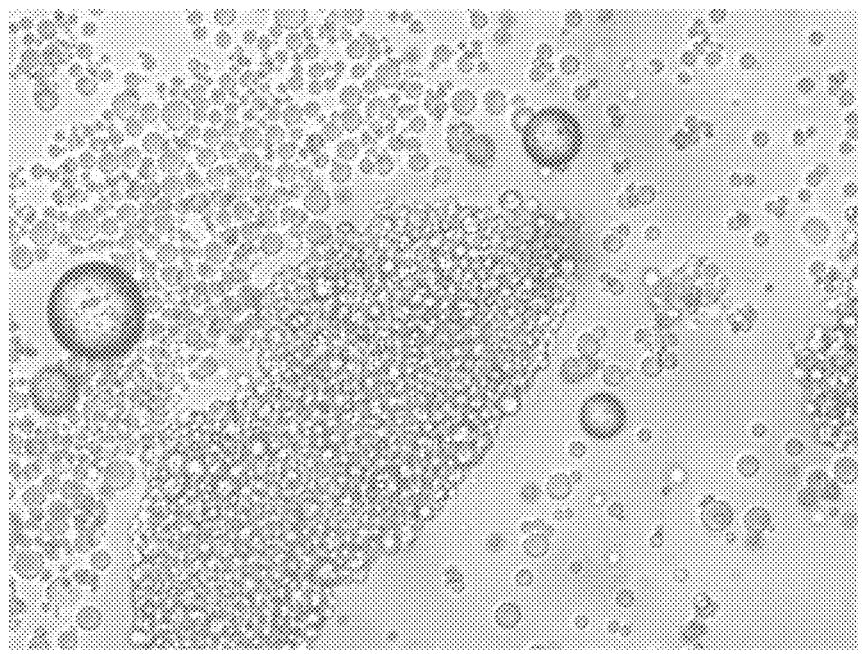
FIG. 10c illustrates that reacting beads with 1,4-CHDDE initially before conjugating the drug yielded very poor results. Beads were seen to extensively clump.
Figure 11A:
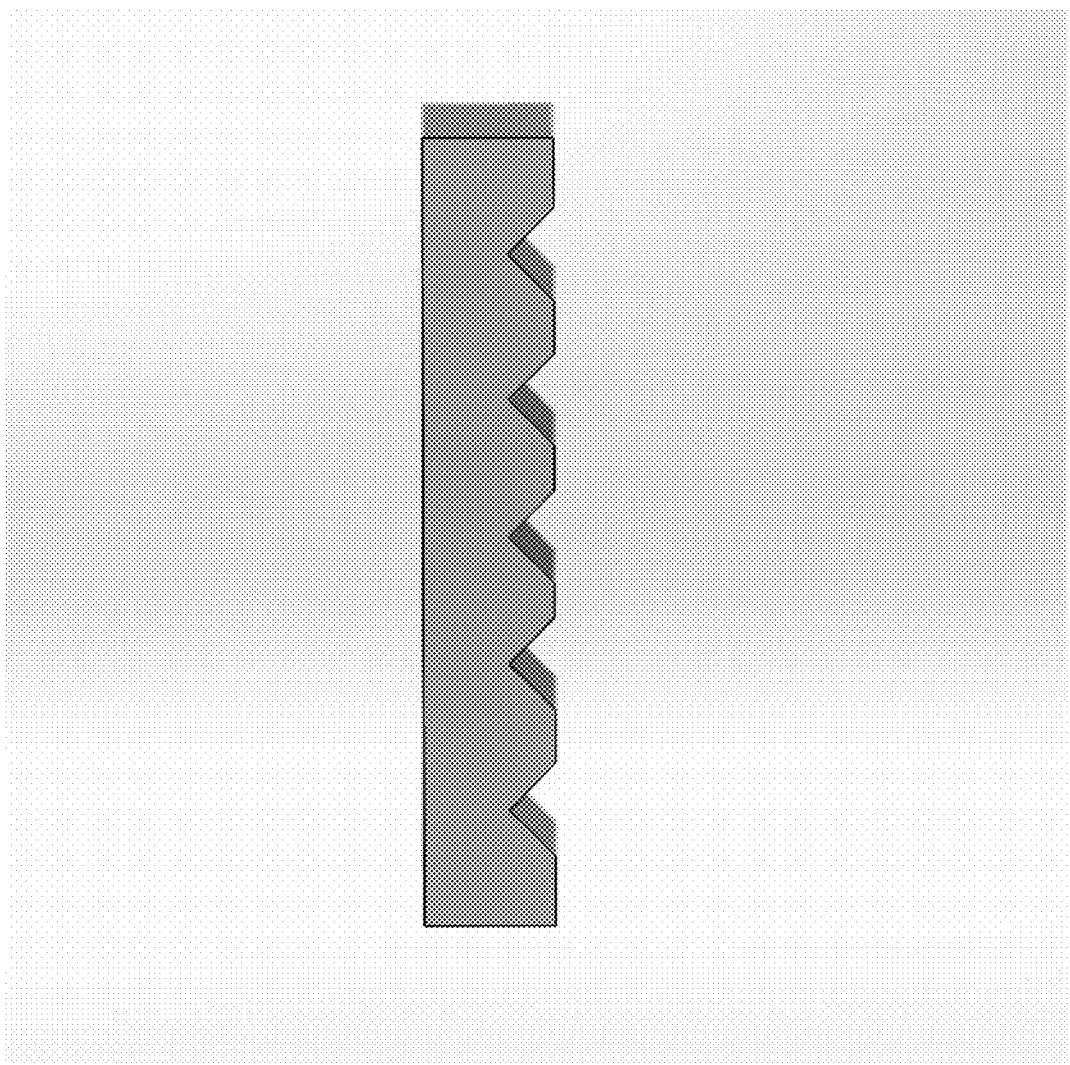
FIGS. 11a, b, c, d, e, f, and g illustrate cuboid geometries for Amikaliths. a)-d) depict mirror pieces separately and joined, while e) depicts an insert that can be joined with pieces in a) and b) (as shown in f and g)
Figure 11B:
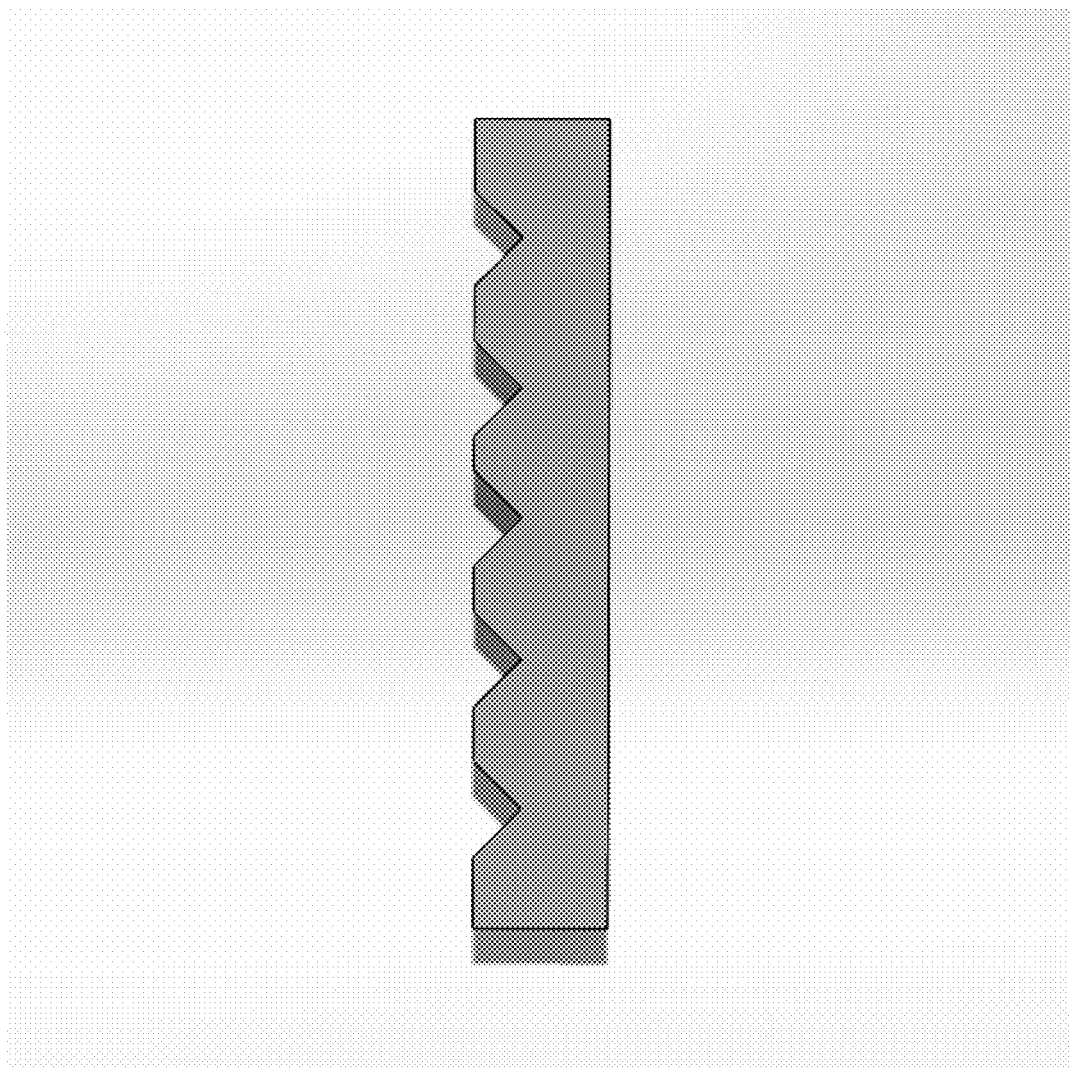
Figure 11C:
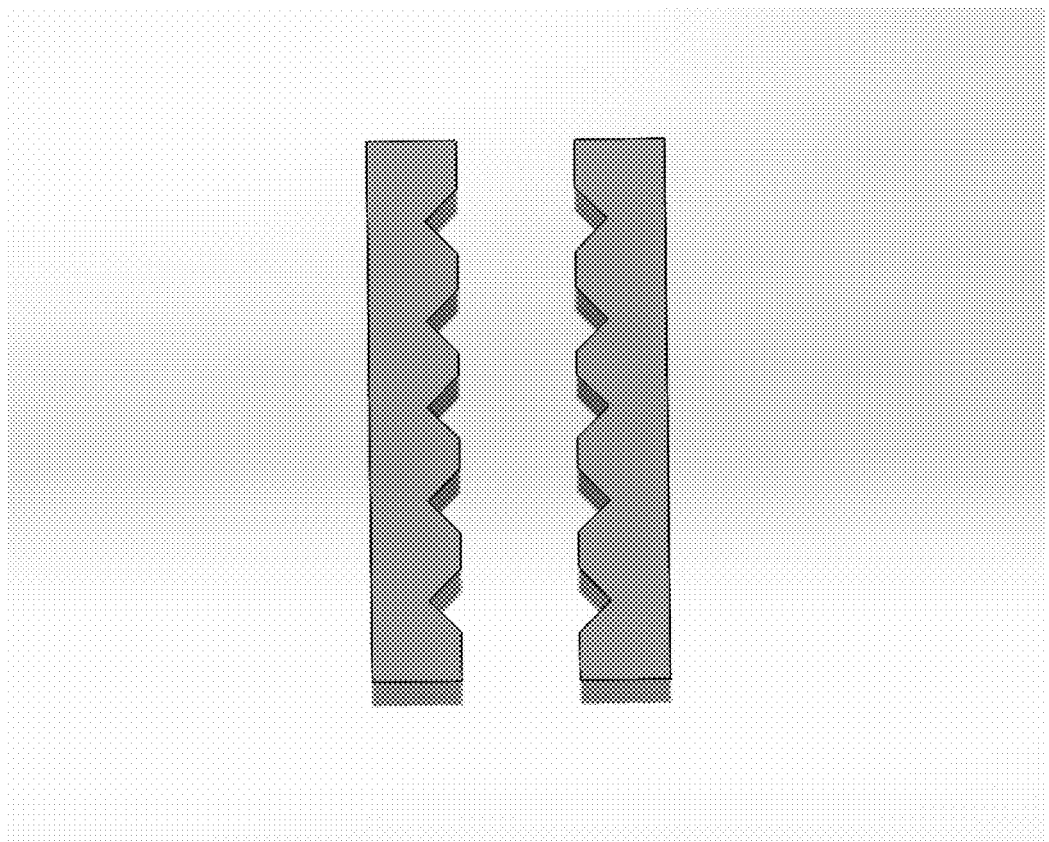
Figure 11D:
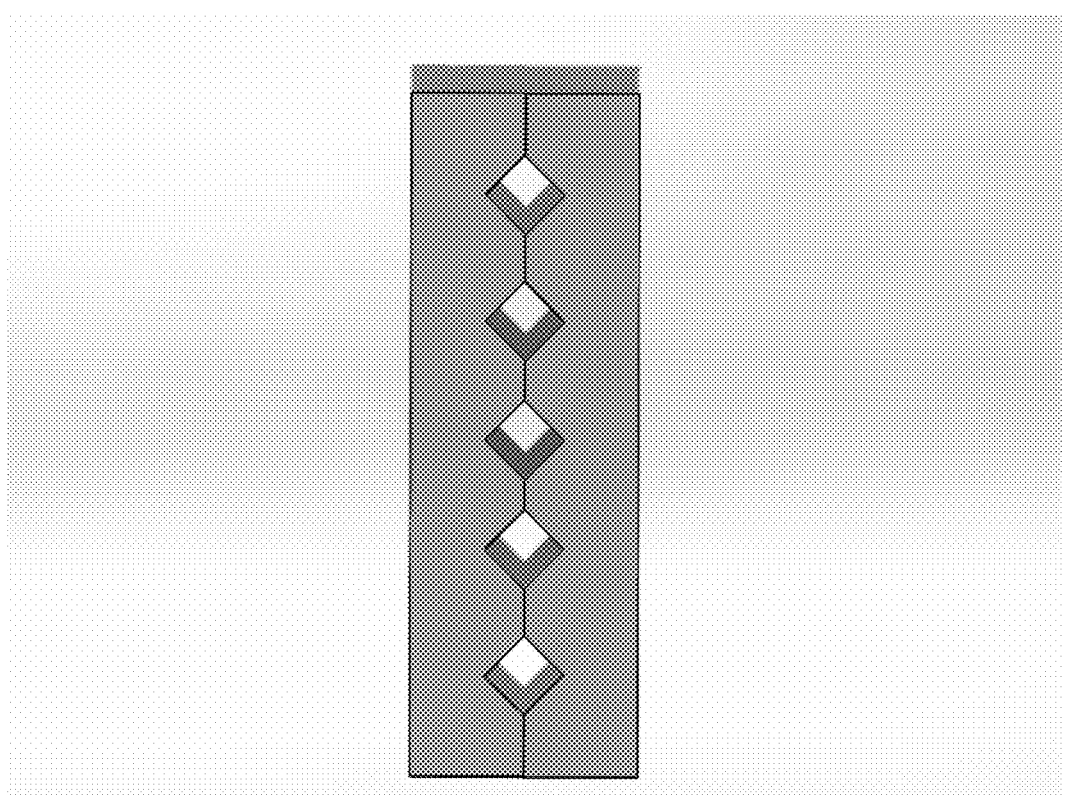
Figure 11E:
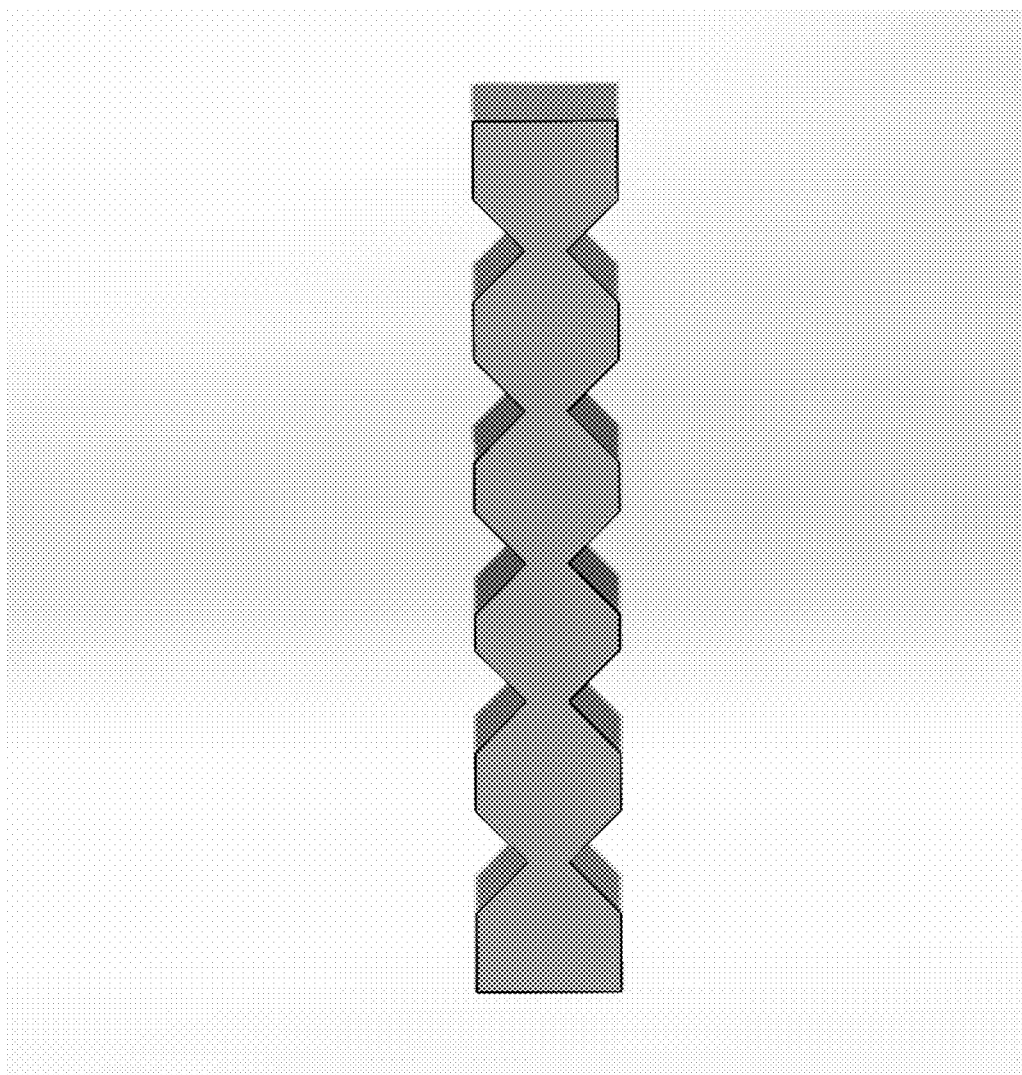
Figure 11F:
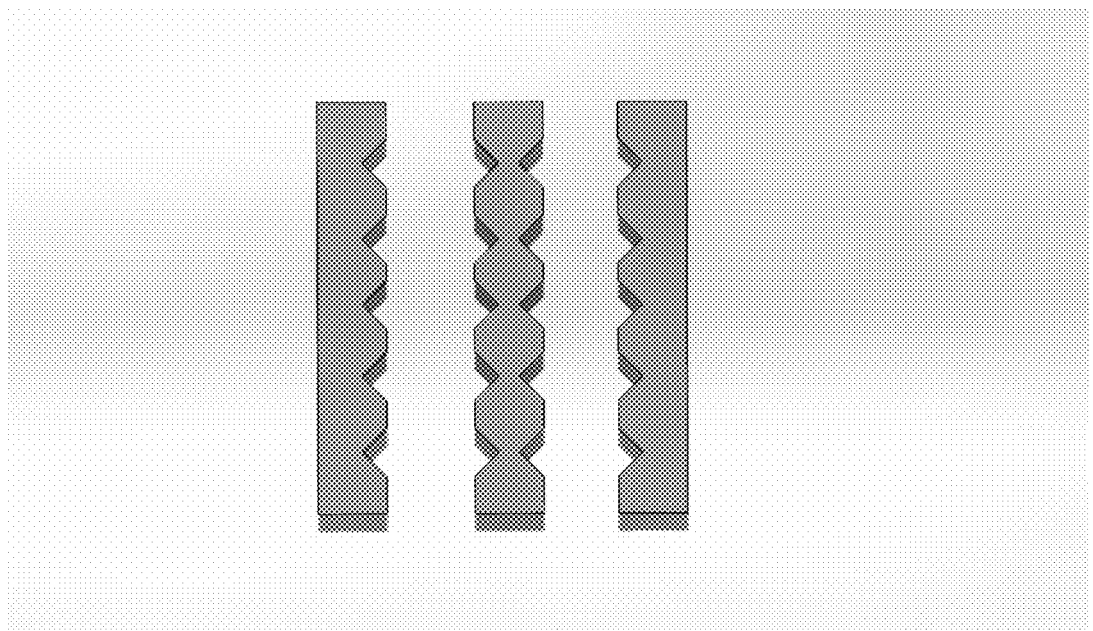
Figure 11G:
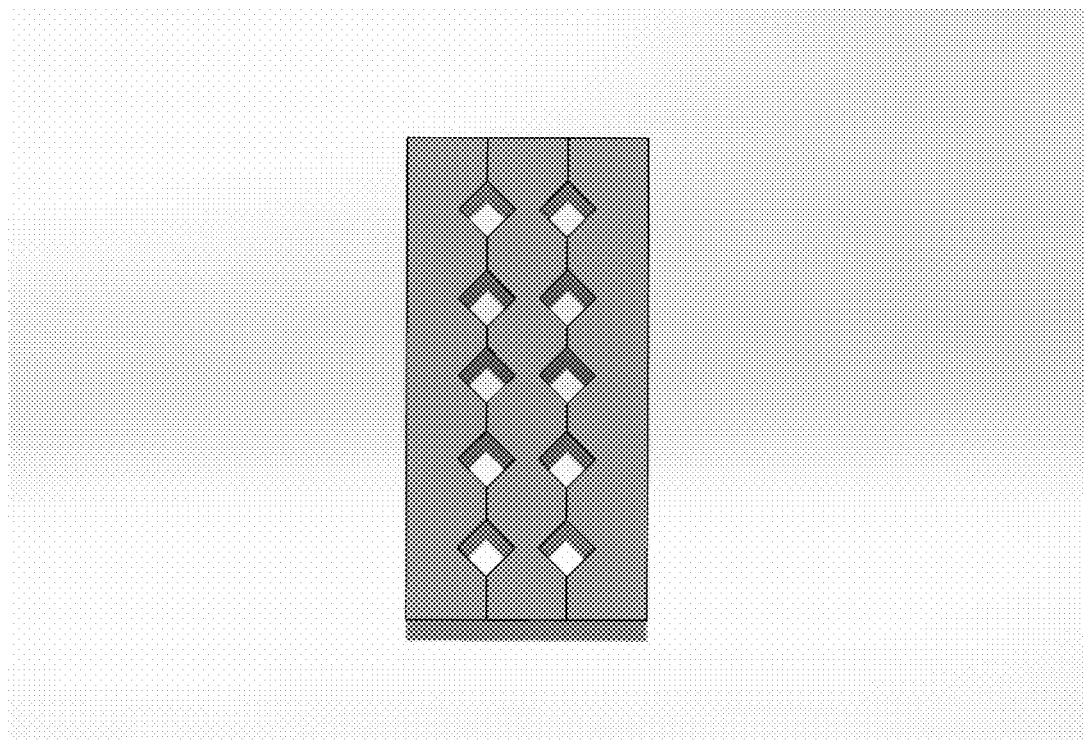

Reversing the protocol by adding excess crosslinker to the beads at the first step did not yield good results. As shown in supporting information, big chunks of cross-linked beads were found when the cross-linker was added to the beads as the first step. Tuning the mole ratio of cross-linker: Amikabeads did not help either (FIG. 10c). Hence, it was hypothesized that working backwards, doxorubicin could be conjugated to one end of the epoxy end of the crosslinker, which could then be added to the intact beads. Applicants propose this is as a better mechanism of conjugating any ligand to the surface of the any microbead.

Conjugation of anticancer drugs to the surface of Amikaliths gives rise to novel materials that can be used for plasmid DNA binding. These DNA binding anticancer drugs could provide multi-modal affinity to the resin to allow increased pDNA binding.

In view of the above, Applicants disclose a novel, scalable, easy-to-use device to generate user defined 3D macroporous polymeric scaffolds in a high-throughput format for their use in substrates for plasmid DNA chromatography, cell culture, stem cell differentiation etc. The device's uniqueness results from a smart design with parafilm coating, in-situ porogen fusion, in-situ polymerization and gelation and breakaway piece design that allow for easy recovery of formed matrices after gelation/polymerization.

The unique design of the device has been tested numerous times to demonstrate its reproducibility. Amikaliths were generated in high throughput and conjugated with DNA binding anticancer drugs. Plasmid DNA was bound to the Amikaliths, which were found to be similar to Amikabeads in their plasmid DNA binding ability. Moreover, multiple geometries for the device are possible (e.g., the cuboid geometry in FIG. 11a-g).

Figure 12:
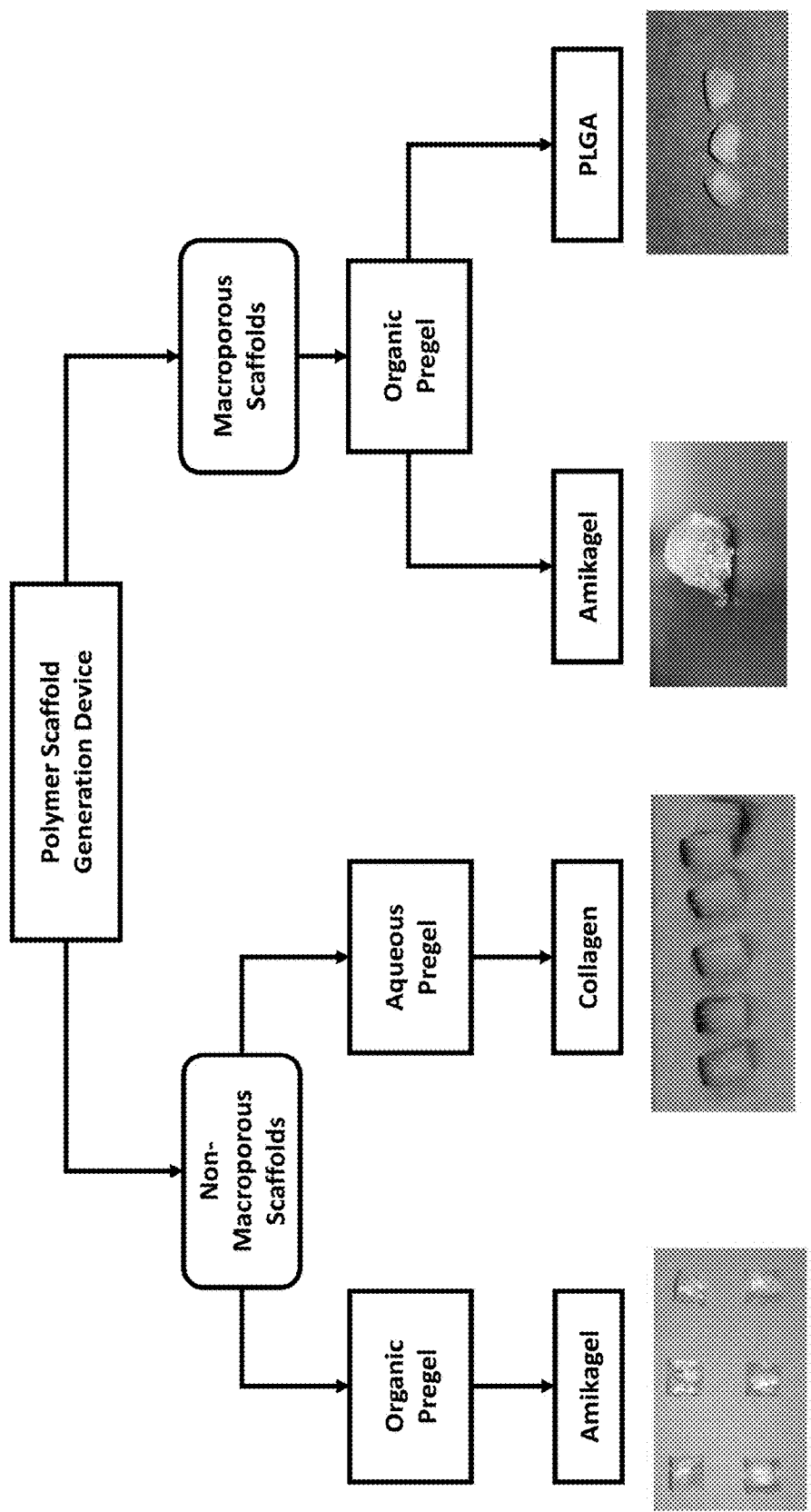
FIG. 12 depicts a flow chart and images of polymer scaffold generation device capabilities.

FIG. 12 depicts a flow chart and images of polymer scaffold generation device capabilities. The acrylic device was used to generate multiple gel types, with organic and aqueous phase pregel, including Amikagel, PLGA and collagen. In addition, both macroporous and non-macroporous morphologies were possible. Non-macroporous gels were formed without the use of a porogen. Successful fabrication of 3D macroporous PLGA matrices demonstrates the current device can be employed to generate multiple user desired polymeric systems. Generation of non-macroporous PLGA monoliths was not attempted, as addition of the chloroform solvent to the acrylic wells would likely cause damage to the device. However, such damage may be avoided by using a non-plastic material to form the device such as wood, glass or steel. Successful fabrication of collagen gels demonstrates the device is not limited to organic phase precursor gels and may be expanded to aqueous phase gels as well. Macroporous collagen gels also may be formed by incorporating an appropriate leachable porogen, such as menthol.

FURTHER EXAMPLE

Amikalith Drip-Flow Binding Protocol

The Polymer scaffold device was hypothesized to serve as an appropriate platform for the binding and elution of plasmid DNA to and from the Amikalith gel. The idea is to flow a buffer suspension containing pDNA through the Amikalith. After an adequate amount of time has passed (allowing pDNA to bind to the Amikalith) fresh buffer is flowed through the Amikalith to wash out any unbound pDNA. An elution buffer is then flowed through the Amikalith to desorb pDNA from the Amikalith through anion-exchange interactions.

Figure 13:
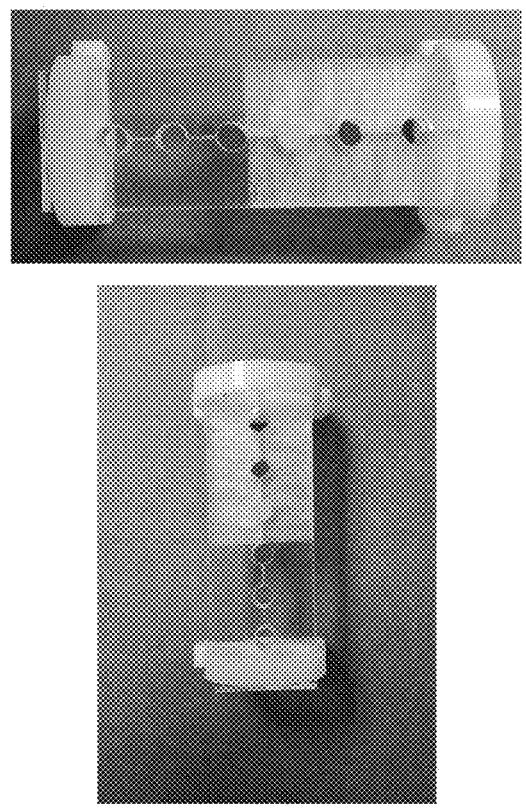
FIG. 13 depicts prototype 6-well device sections wrapped, joined with clamps, and with a parafilm base applied to bottom. These prototypes are used in the "Further Example."

A special 6-well device (FIG. 13) was created with slightly wider wells (0.3 inch diameter) than the device previously used to form the Amikalith. This is because the gels expand upon hydration and would get crushed if confined within the wells they were formed in. By placing them in a slightly wider well, the wetted columns tightly hug the walls of the device while still allowing transport of liquid through the Amikalith. The following materials and methods were employed.

Materials:
Amikaliths (10 µL 1 hour Salt Fused)
6-well acrylic device
Nanopure water (NPW)
Plasmid DNA (PGL-4.5)
EB Buffer
Elution Buffer:
950 mM NaCl, 50 mM Tris-Cl, 15% isopropyl alcohol, pH 8.5, 60° C. supernatant
Clamps
Methods:
Device Set-Up:
6-well device sections wrapped in parafilm, joined, parafilm base applied to bottom
Clamps placed on either end of device to serve as stand
Cotton stick (bare end) to poke hole in parafilm base under each well
Amikalith (salt-gel matrix) placed in each well
Amikaliths are washed with 5 mL NPW each to dissolve & wash away salt. Gently remove remaining NPW from well using pipette. Mix desired concentration of pDNA in EB buffer in separate container so total volume ~50 µL. Then add pDNA/buffer suspension to wells containing Amikaliths and let sit 5 hours.

After 5 hr, wash Amikaliths w/4 mL EB buffer each (collect post-flowed buffer from each well in a separate container). Measure pDNA concentrations in post-flowed buffer solutions, and mass balance to determine amount of pDNA bound to each Amikalith, i.e.: pDNA bound=Total pDNA added−pDNA in post-flowed buffer solution. Next, flow 4 mL elution buffer through each well containing Amikalith column (collect post-flowed buffer from each well in a separate container), and measure desorbed pDNA concentrations in post-flowed buffer solutions. Mass balance to determine amount of pDNA recovered from Amikaliths, i.e.: pDNA % recovered=(pDNA in post-flowed buffer/pDNA bound)×100%.

The methods described above were tested using buffers with varying concentrations of pDNA. Amikaliths initially loaded with 15,000 ng, 45,000 ng and 60,000 ng of pDNA were observed to bind 5,940 ng, 20,430 ng and 24,835 ng respectively. Following addition of the elution buffer, Amikaliths were observed to elute approximately 100%, 45% and 35% of bound pDNA respectively.

While the preferred embodiments of the present invention have been illustrated in detail, it should be apparent that modifications and adaptations to those embodiments may occur to one skilled in the art without departing from the scope of the present invention.

What is claimed is:

1. A method for generating a three-dimensional polymeric scaffold in high-throughput in-situ utilizing a substrate with a cavity, comprising:
   adding monomers and a porogen in said cavity; and
   initiating polymerization in-situ to thereby form said scaffold in said substrate cavity.

2. The method of claim 1, wherein said porogen comprises a salt fusion column and said monomers are added to said column.

3. The method of claim 1, wherein said porogen is selected from the group consisting of one or more of a salt and a sugar.

4. The method of claim 1, wherein said cavity is formed to produce said three-dimensional polymeric scaffold in a cuboid or spherical shape.

5. The method of claim 1, wherein said substrate comprises acrylic.

6. The method of claim 1, wherein said substrate is selected from the group consisting of one or more of wood, steel, glass, or polypropylene.

7. The method of claim 1, further including providing a bottom layer of a waterproof film to said substrate.

8. The method of claim 1, wherein said monomers are selected from the group consisting of one or more of a collagen, a fibronectin, a PLGA, and a peptide gel.

9. The method of claim 1, further including a step of adding a pseudoaffinity ligand to a surface of a polymerized scaffold.

10. The method of claim 9, wherein said pseudoaffinity ligand comprises Doxorubicin.

11. A method for generating a polymeric scaffold in high-throughput utilizing at least two substrates that are joined to form one or more cavities and then disjoined to enable the removal of said scaffold, comprising:
    adding monomers in said one or more cavities; and
    initiating polymerization to thereby form said scaffold, whereby said at least two substrates are disjoined after polymerization to enable removal of said polymeric scaffold.

12. The method of claim 11, further including with said monomers a porogen selected from the group consisting of one or more of a salt and a sugar.

13. The method of claim 12, wherein said porogen comprises a salt fusion column.

14. The method of claim 11, wherein said one or more cavities are formed to produce said three-dimensional polymeric scaffold in a cuboid or spherical shape.

15. The method of claim 11, wherein said substrates comprises acrylic.

16. The method of claim 1, wherein said substrates are selected from the group consisting of one or more of wood, steel, glass, or polypropylene.

17. The method of claim 11, further including providing a bottom layer of a waterproof film to said substrates.

18. The method of claim 11, wherein said monomers are selected from the group consisting of one or more of a collagen, a fibronectin, a PLGA, and a peptide gel.

19. The method of claim 11, further including a step of adding a pseudoaffinity ligand to a surface of a polymerized scaffold.

20. The method of claim 19, wherein said pseudoaffinity ligand comprises Doxorubicin.

* * * * *